United States Patent [19]

Kuusela et al.

[11] Patent Number: 5,496,706
[45] Date of Patent: Mar. 5, 1996

[54] **METHODS AND MATERIALS FOR THE DETECTION OF *STAPHYLOCOCCUS AUREUS***

[75] Inventors: Pentti Kuusela; Pekka Hilden, both of Helsinki, Finland

[73] Assignee: Helsinki University Licensing, Ltd., Helsinki, Finland

[21] Appl. No.: 169,524

[22] Filed: Dec. 17, 1993

[51] Int. Cl.$^6$ .................. G01N 33/569; G01N 33/536; G01N 33/577
[52] U.S. Cl. .................. 435/7.33; 435/7.32; 435/883; 435/975; 436/547; 530/388.4; 530/389.5
[58] Field of Search .................. 435/7.33, 7.32, 435/975; 436/547, 548; 530/388.4, 389.5, 391.1, 413; 424/87

[56] References Cited

FOREIGN PATENT DOCUMENTS

89/02077 3/1989 WIPO.

OTHER PUBLICATIONS

Kuusela et al, "Rapid Detection of Methicillin–Resistant *Staphylococcus aureus* Strains Not Identified by Slide Agglutination Tests", J. Clin. Microbiol., 32(1):143–147 (Jun. 1994).
Aldridge, et al., "Comparison of Rapid Identification Assays for *Staphylococcus aureus*," J. Clin. Microbiol., 19(5):703–704 (May, 1984).
Baker, et al., "Evaluation of Various Rapid Agglutination Methods for the Identification of *Staphylococcus aureus*," J. Clin. Microbiol., 21(5):726–729 (May, 1985).
Berger–Bächi et al., "FfemA, a host–mediated factor essential for methicillin resistance in *Staphylococcus aureus*: Molecular cloning and characterization," Mol. Gen. Genet., 219:263–269 (1989).
Berke and Tilton, "Evaluation of Rapid Coagulase Methods for the Identification of *Staphylococcus aureus*," J. Clin. Microbiol. 23(5):916–919 (May, 1986).
Blair & Williams, "Phage Typing of Staphylococci," Bull. Wld. Hlth. Org., 24:771–784 (1961).
Brown, "Comparison of a Yellow Latex Reagent with Other Agglutination Methods for the Identification of *Staphylococcus aureus*," J. Clin. Microbiol., 23(3):640–642 (Mar., 1986).
Eskola, et al., "A Randomized, Prospective Trial of a Conjugate Vaccine in the Protection of Infants and Young Children Against Invasive *Hemophilus influenzae* type b Disease," N. Eng. J. Med., 323(20):1381–1387 (1990).
Essers and Radebold, "Rapid and Reliable Identification of *Staphylococcus aureus* by a Latex Agglutination Test," J. Clin. Microbiol., 12(5):641–643 (Nov., 1980).
Fournier et al., "New Latex Reagent Using Monoclonal Antibodies to Capsular Polysaccharide for Reliable Identification of Both Oxacillin–Susceptible and Oxacillin–Resistant *Staphylococcus aureus*," J. Clin. Microbiol., 31(5):1342–1344 (May, 1993).
Guzman et al., "Novel Immunoenzymatic Assay for Identification of Coagulase– and Protein A–Negative *Staphylococcus aureus* Strains," J. Clin. Microbiol., 30(5):1194–1197 (May, 1992).
Kloos and Lambe, "Staphylococcus," Manual of Clinical Microbiology, pp. 222–237, (Balows et al., eds.) (1991).
Kuusela, "Fibronectin binds to *Staphylococcus aureus*," Nature, 276:718–720 (Dec. 14, 1978).
Laemmli, "Cleavage of Structural Proteins during the Assembly of the Head of Bacteriophage T4," Nature, 227:680–685 (Aug. 15, 1970).
Lairscey and Buck, "Performance of Four Agglutination Methods for Identification of *Staphylococcus aureus* When Testing Methicillin–Resistant Staphylococci," J. Clin. Microbiol., 25(1):181–182 (Jan., 1987).
Lopes et al., "Presence of Laminin Receptors in *Staphylococcus aureus*," Science, 229:275–277 (Jul. 19, 1985).
Lowry et al., "Protein Measurement With the Folin Phenol Reagent," J. Biol. Chem., 193:265–275 (1951).
Niskanen et al., "Evaluation of Three Slide Agglutination Tests for Rapid Identification of *Staphylococcus aureus*," Acta Vet. Scand., 32:543–549 (1991).
Piper et al., "Efficacies of Rapid Agglutination Tests for Identification of Methicillin–Resistant Staphylococcal Strains," J. Clin. Mlcrobiol., 26(9):1907–1909 (Sep., 1988).
Ruane et al., "Failure of Rapid Agglutination Methods to Detect Oxacillin–Resistant *Staphylococcus aureus*," J. Clin. Microbiol. 24(3):490–492 (Sep., 1986).
Speziale et al., "Binding of Collagen to *Staphylococcus aureus* Cowan 1," J. Bacteriol., 167(1):77–81 (Jul., 1986).
Towbin, et al., "Electrophoretic transfer of proteins from polyacrylamide gels to nitrocellulose sheets: Procedure and some applications," Proc. Natl. Acad. Sci. (USA), 76(9):4350–4354 (Sep., 1979).
Ubukata et al., "Occurrence of a β–Lactam–Inducible Penicillin–Binding Protein in Methicillin–Resistant Staphylococci," Antimicrob. Agents Chemother., 27(5):851–857 (May, 1985).
Wanger et al., "Latex Agglutination–Negative Methicillin–Resistant *Staphylococcus aureus* Recovered from Neonates: Epidemiologic Features and Comparison of Typing Methods," J. Clin. Microbiol. 30(10):2583–2588 (Oct., 1992).
Woolfrey et al., "An Evaluation of Three Rapid Coagglutination Tests: Sero–STAT, Accu–Staph and Staphyloslide, for Differentiating *Staphylococcus aureus* from Other Species of Staphylococci," Am. J. Clin. Pathol. 81(3):354–348 (1984).

Primary Examiner—Toni R. Scheiner
Assistant Examiner—Nancy J. Parsons
Attorney, Agent, or Firm—Marshall, O'Toole, Gerstein, Murray & Borun

[57] ABSTRACT

The present application discloses a novel method for the detection of *Staphylococcus aureus* and methicillin-resistant strains of *Staphylococcus aureus*. Further disclosed is an approximately 230 kDa protein and the use of such protein in detection assays for *Staphylococcus aureus* and in other diagnostic applications.

6 Claims, 3 Drawing Sheets

METHODS AND MATERIALS FOR THE DETECTION OF *STAPHYLOCOCCUS AUREUS*

FIELD OF THE INVENTION

The present invention generally relates to methods for the detection of the bacterium, *Staphylococcus Aureus*, and materials related thereto.

BACKGROUND OF THE INVENTION

*Staphylococcus aureus* is a gram-positive facultative aerobe which is considered among the most virulent species of the genus. It is part of the bacterial flora indigenous to humans. A *Staphylococcus aureus* infection may result when injury occurs to the skin or protective mucous membranes, thus allowing invasion of the bacterium. Epidermal infection is the most common form of Staphylococcus infection in humans. However, *Staphylococcus aureus* is also a common organism isolated from patients with nosocomial pneumonia.

When introduced in food, *Staphylococcus aureus* may produce one or more staphylococcal enterotoxins. If ingested, heat stable Staphylococcal enterotoxins may produce symptoms of food poisoning and a range of other diseases.

*Staphylococcus aureus* possesses a resistant cell wall which comprises a cross-linked peptidoglycan layer which may protect the cell from invasion by the host. In addition, the cell wall is resistant to phagocytosis which is thought to be due, in part, to the production of Protein A on the cell surface. *Staphylococcus aureus* also produces hemolytic toxin which may damage blood cells and immune cells.

Treatment of *Staphylococcus aureus* infections generally comprises the use of penicillin, erythromycin, or methicillin. However, numerous strains have emerged which are resistant to penicillin and, recently, others have been found which are methicillin-resistant. These methicillin-resistant strains are usually resistant to most other anti-microbial drugs and therapy in response to a methicillin resistant strain usually requires administration of a more potent antibiotic, such as vancomycin.

Of interest to the field as well as to the present invention, are laboratory tests to identify *Staphylococcus aureus* infection and, in particular, methicillin-resistant strains which may not be detected by traditional assays and may be unresponsive to traditional therapy. Assays for *Staphylococcus aureus* typically are based upon (1) a coagulation assay, measuring coagulation of test serum to appropriately prepared rabbit plasma; (2) observation of the morphology of the suspected pathogen; (3) detection of the production of thermostable nucleases; and (4) the utilization by the pathogen of specific sugars as carbohydrate sources. Kloos, et al., *Manual of Clinical Microbiology*, 222–237 (Balows, et al., eds. 1991). Such traditional methods suffer from serious drawbacks. Traditional assays for *S. aureus* require several hours of incubation and may provide ambiguous results. Slide agglutination assays have been developed which may overcome some of those problems. Aldridge, et al., *J. Clin. Microbiol.*, 19: 703–704 (1984); Baker et al., *J. Clin. Microbiol.*, 21: 726–729 (1985); Berger-Bächi, et al., *Mol. Gen. Genetics*, 219: 263–269 (1989). Such assays involve particles coated with fibrinogen or fibrinogen and an IgG immunoglobulin. Fibrinogen-binding protein (clumping factor) and protein A, both associated with the cell surface of *S. aureus*, bind to the coated particles, resulting in a positive assay. However, reports indicate that most such assays are not capable of detecting certain methicillin-resistant *S. aureus*. Berger-Bächi, Supra; Laircsey, et al., *J. Clin. Microbiol.*, 25: 181–182 (1987); Piper, et al., *J. Clin. Microbiol.*, 26: 1907–1909 (1988); Wagner, et al., *J. Clin. Microbiol.*, 30: 2583–2588 (1992).

Failure to detect methicillin-resistant strains may result in misdiagnosis and/or improper therapy. Also, to control the spread of *S. aureus*-related diseases and to determine the source of an outbreak of *S. aureus* infection, proper and precise identification of the bacterium, including the strain, is essential.

Accordingly, there is a need in the art for rapid, reliable means for detecting all methicillin-resistant strains of *Staphylococcus aureus*, as provided in the present invention

SUMMARY OF THE INVENTION

The present invention provides an approximately 230 kDa protein, designated MRSA-230, which is isolated from lysostaphin digests of methicillin-resistant *Staphylococcus aureus* which test negative in standard *S. aureus* agglutination assays. Anti-MRSA-230 Antibodies or antisera comprising the antibodies are useful, inter alia, in methods for the detection of *Staphylococcus aureus* generally and are especially useful for detection of methicillin-resistant strains of *Staphylococcus aureus* which are not detected by standard slide agglutination assays. The MRSA-230 protein, or fragments of that protein which retain MRSA-230 biological activity, are also useful in vaccine compositions which promote an immune response to MRSA-230 and, thus, to *Staphylococcus aureus*.

Detection of *S. aureus* according to the present invention is accomplished using a sample of *S. aureus* obtained from any source including, but not limited to, blood, tissue, ascites, pus, urine, and feces. Samples may also be obtained for detection from food; from surfaces, such as floors, tables, and the like; and from airborne particles, such as pollen and dust.

Accordingly, the present application provides a method for the detection of *S. aureus*, comprising the steps of exposing one or more samples suspected of containing an *S. aureus* to a composition comprising anti-MRSA-230 antibodies; and selecting samples which form agglutination products with said antibodies.

In a preferred embodiment of the invention, anti-MRSA-230 antibodies are obtained from immunized rabbit serum by methods known to one of ordinary skill in the art. Also in a preferred embodiment, the sample suspected of containing *S. aureus* is blood, pus, or ascites.

A *Staphylococcus aureus* to be detected by the methods of the present invention may be a methicillin-resistant strain of *S. aureus* or may be resistant to another antimicrobial drug, or combination of antimicrobial drugs.

A purified MRSA-230 protein, or biologically-active fragment, is provided by the present invention. The skilled artisan recognizes that fragments of MRSA-230 are those which retain sufficient biological properties to elicit an anti-MRSA-230 immune response or to be effective as a vaccine against *S. aureus*.

Anti-MRSA-230 antibodies may be either monoclonal antibodies or polyclonal antibodies produced by well-known methods in the art. See, e.g., Harlow, et al., *Antibodies A Laboratory Manual* (Cold Spring Harbor Laboratory Press, 1988).

A kit according to the present invention contains a formulation of anti-MRSA-230 antibody to be applied to a sample suspected of containing *S. aureus* or a methicillin-resistant *S. aureus*.

A pharmaceutical composition according to the invention comprises an MRSA-230 protein or fragment thereof in a pharmaceutically-acceptable carrier.

Proteins according to the invention, MRSA-230 and fragments, are useful in generating an immune response directed against *S. aureus*. Antibodies of the invention are useful as inhibitors of reactions mediated by *S. aureus* and as components of *S. aureus* detection methods.

Additional aspects of the invention will become apparent to the skilled artisan upon consideration of the detailed description which follows.

DETAILED DESCRIPTION OF THE INVENTION

Figure 1A:
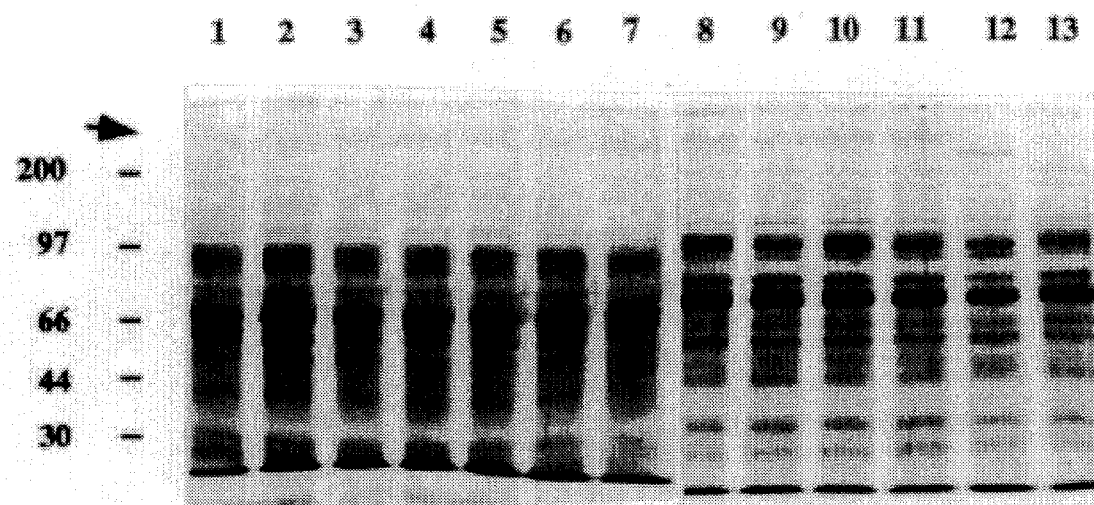
FIGS. 1A and 1B show gels obtained from SDS-PAGE analysis of lysostaphin digests of various MRSA-aggl⁻ and agglutination-positive strains, respectively, which were stained for protein.

The present invention relates to methods for detection of *Staphylococcus aureus*, and particularly to detection of methicillin-resistant *Staphylococcus aureus* which are not detected by standard agglutination assays and to the use of an approximately 230 kDa protein, or biologically-active fragment thereof, in methods for detection of *S. aureus* and in vaccines and pharmaceuticals for the prevention of *S. aureus* and diseases caused by *S. aureus*. Methods according to the invention provide a rapid, accurate, and more complete, means for detecting and identifying *S. aureus*, and especially a method of detecting all methicillin-resistant *S. aureus*, than are found in the art. In the present application, strains of *S. aureus* which are negative in standard agglutination tests (i.e., tests designed to detect the surface-associated protein A and/or clumping factor) are referred to as "MRSA-aggl⁻", including methicillin-resistant strains which test negative in standard slide agglutination tests.

EXAMPLE 1

Isolation of *Staphylococcus aureus* strains and determination of antimicrobial susceptibility and phage typing Various samples of *Staphylococcus aureus* were obtained to determine the efficacy of methods for *S. aureus* detection according to the art and according to the present invention. A total of 79 methicillin-resistant *S. aureus* (MRSA) strains were collected as clinical samples originating from 12 different hospitals and clinics in Finland. In order to minimize the possibility of obtaining the same bacterial strain from different patients, a period of at least three months was required between the isolation of samples originating from the same hospital or clinic. Twenty methicillin-sensitive *S. aureus* strains were collected each year as controls for slide agglutination tests. All strains were stored in milk-glycerol (1 L contained 40.0 g milk powder, 140 ml glycerol, and 850 ml water) at −70° C. and cultivated on sheep blood agar plates for 20–24 hours at 37° C. prior to testing. Further, all strains were coagulase, deoxyribonuclease, and urease producers and were capable of forming acid from maltose and trehalose. Strains which gave a negative result in MRSA agglutination tests were identified as *S. aureus* by an API-Staph™ assay (Biomerieux).

Antimicrobial susceptibility of subject *S. aureus* strains was determined with Neo-sensitabs™ disks (A/S Rosco) and Mueller-Hinton II medium (BBL, Becton-Dickinson Microbiology Systems). Methicillin resistance was determined with 1 mg oxacillin discs on Mueller-Hinton agar plates (BBL, Cockeysville, Md., a one liter plate contained 2.0 g beef extract, 17.5 g casein hydrolysate, 1.5 g starch, and 17.0 g agar) which were incubated at 30° C.

Minimal inhibitor concentration (MIC) values for oxacillin were determined by plate dilution on Mueller-Hinton II agar plates with 4% NaCl under 37° C. incubation. Strains having an MIC for oxacillin of greater than or equal to 4 mg/ml were regarded as methicillin resistant. Similar methods known to the skilled artisan may be used to determine the susceptibility of strains to other antimicrobial compounds.

Phage typing was performed using the International Phage Set according to Blair, *Bull. World. Health Org.*, 24: 771– 784 (1961), incorporated by reference herein.

Susceptibility of isolated MRSA-aggl⁻ strains to various antibiotics is shown in Table 1. Strains were shown to represent five different types, consisting of two phage types (strains a, b, c, which belong to phage type 81/42E/47/54/75/84/85; and strains d and e, belonging to phage type 85, as reported in Blair, et al., *Bull. World Health Org.*, 24: 771–784 (1961)). Neither phage type was common to any strains which produced positive MRSA agglutination results.

TABLE 1

| | Antibiotic Resistance of MRSA-aggl⁻ Strains | | | |
|---|---|---|---|---|
| Strain | No. Isolates | Erythromycin | Clindamycin | Tobramycin |
| a | 4 | R | R | R |
| b | 1 | S | S | R |
| c | 2 | S | S | S |
| d | 2 | R | R | R |
| e | 5 | R | S | R |

In Table 1, R denotes resistance to the indicated antibiotic and S denotes sensitivity to the indicated antibiotic.

EXAMPLE 2

Characterization of MRSA Strains

Antiserum against MRSA strains which tested negative in standard agglutination tests according to the art (MRSA-aggl⁻) was prepared by immunizing rabbits with 10⁹ heat-killed MRSA-aggl⁻ bacterial cells in 0.5 ml Freund's complete adjuvant by three subcutaneous injection at two-week intervals. Ten days after the final booster injection, blood was collected by heart puncture and the serum isolated. The antiserum was absorbed twice with intact *Staphylococcus epidermidis* (ATCC Accession No. 12228), using 2×10⁹ bacteria per milliliter antiserum for 2 hours at 4° C. grown on Todd-Hewitt broth (BBL, one liter contained 3.1 g beef heart infusion, 20.0 g peptone, 2.0 g dextrose, 2.0 g NaCl, 0.4 g Di-Na-phosphate, 2.5 g Na-carbonate)

Agglutination tests were performed by cultivating methicillin-resistant *S. aureus* strains on sheep blood agar plates overnight at 37° C. The slide agglutination test, Staphyslide- Test™ (BioMeriux), was used. That test is a hemagglutination test employing fibrinogen-coated or uncoated (control) sheep red blood cells in order to detect clumping factor on *S. aureus* (i.e., agglutination, a positive test result). Also employed were a Staphaurex™ (Wellcome Diagnostics) assay or an ANI *S. aureus* TEST™ (Ani Biotech Oy, Finland) assay, both of which are latex agglutination assays in which particles are coated with fibrinogen and immunoglobulin G in order to detect *S. aureus* clumping factor or protein A, respectively. All of the assays were conducted according to the manufacturer's instructions.

Eleven of the 79 strains obtained tested negative in the above-mentioned agglutination assays and three strains displayed variable results, but were included as MRSA-aggl⁻ strains. The proportion of MRSA-aggl⁻ strains was 17.7% (14/79, See Table 1). There was no statistically-significant difference (Student's T-test) between the MIC values for oxacillin in MRSA-aggl⁻ and positively-agglutinating cells.

EXAMPLE 3

Isolation of 230 KDa Protein From MRSA-aggl⁻ Strains

MRSA strains were subjected to lysostaphin digestion and analysis to determine the composition of membrane surface-bound proteins which might act as antigens in *S. aureus* agglutination detection assays. Strains were grown on Todd-Hewitt broth overnight at 37° C. and then collected by centrifugation and washed twice with phosphate-buffered saline (PBS). Bacterial density was adjusted to approximately $2 \times 10^{10}$ bacterial cells/ml. Digestion was accomplished by incubating 0.5 ml bacterial suspension for 2 hours at 37° C. with 10 μg recombinant lysostaphin (Applied Microbiology, New York, N.Y.), 4 μg RNAase, and 4 μg DNAase (Sigma, St. Louis, Mo.). Unbroken bacterial cells were removed by centrifugation and the supernatants were incubated for 15 minutes at 80° C. to inhibit enzyme activity. Finally, protein concentration in the digests was determined as reported in Lowry, et al., *J. Biol. Chem.*, 193: 265–275 (1951).

Lysostaphin digests were then run on standard SDS-PAGE using slabs containing 8% acrylamide according to a procedure described in Laemmli, *Nature*, 277:680–685 (1970). Other SDS-PAGE procedures are known to the skilled artisan. The resulting gels were stained with Coomassie blue for protein and, when necessary, subsequently transferred electrophoretically to nitrocellulose membranes according to a procedure reported in Towbin, et al., *Proc. Nat. Acad. Sci.* (USA), 76:4350–4354 (1979). Membranes were pretreated for one hour at room temperature with PBS containing 5% (weight per volume) defatted milk powder and 1% (weight per volume) Triton X-100. They were then washed with TEN-Tween buffer (0.05M Tris-HCl, pH 7.5, 0.025M EDTA, 0.15M NaCl, 0.5% Tween 20). The membranes were first probed with an anti-MRSA-aggl⁻ antiserum or control serum diluted 1:200 and subsequently with horseradish peroxidase-conjugated F(ab)'$_2$ fragments of sheep anti-IgG antibodies (Jackson ImmunoResearch), both diluted in TEN-Tween buffer. Finally, membranes were washed four times with TEN-Tween buffer and once with PBS. The resulting bands were visualized by incubating membranes in 50 ml of 50 mM acetate buffer, pH 5.0, containing 10 mg of 3-amino-9-ehtylcarbazole, 2.5 ml N,N-dimethylformamide, and 30% hydrogen peroxide (30 μl).

Figure 1B:
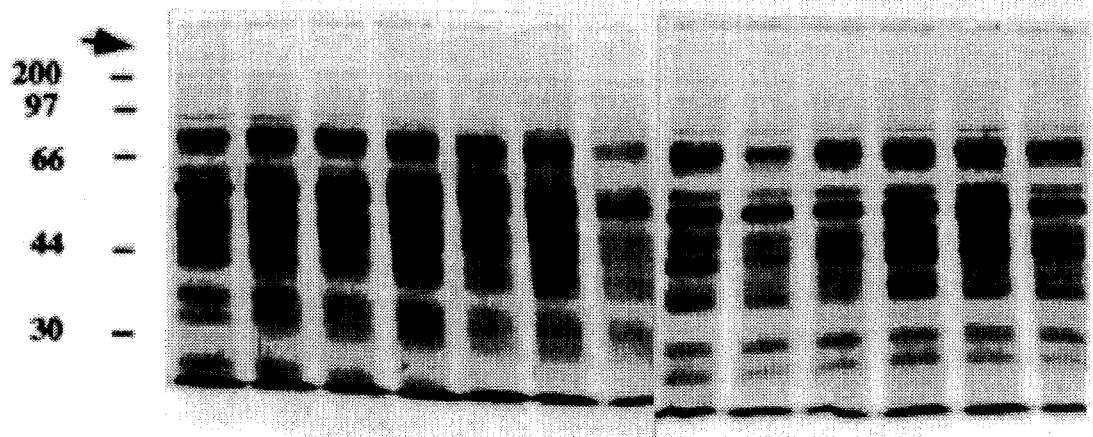
Figure 2A:
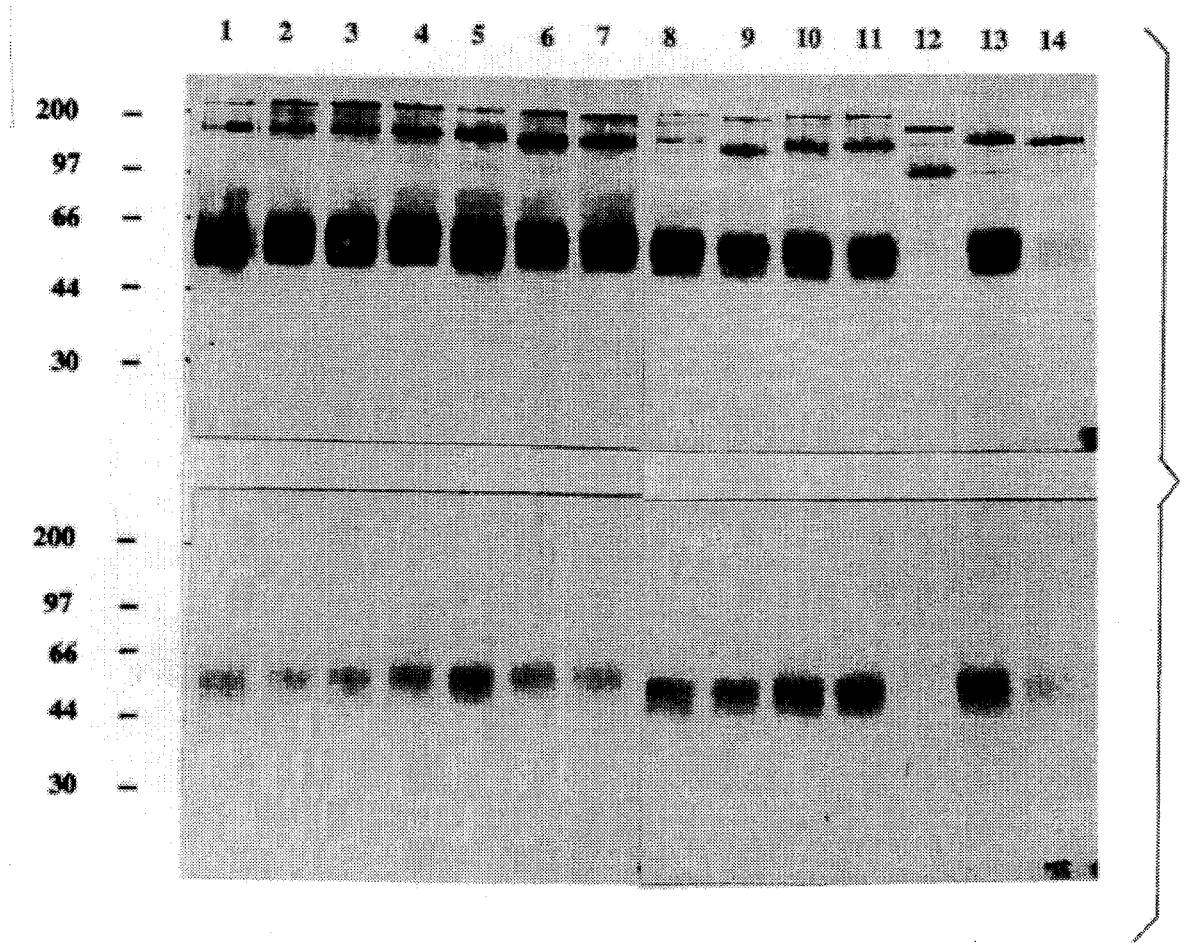
FIGS. 2A and 2B show the results of immunoblots of lysostaphin digests of MRSA-aggl⁻ strains.
Figure 2B:
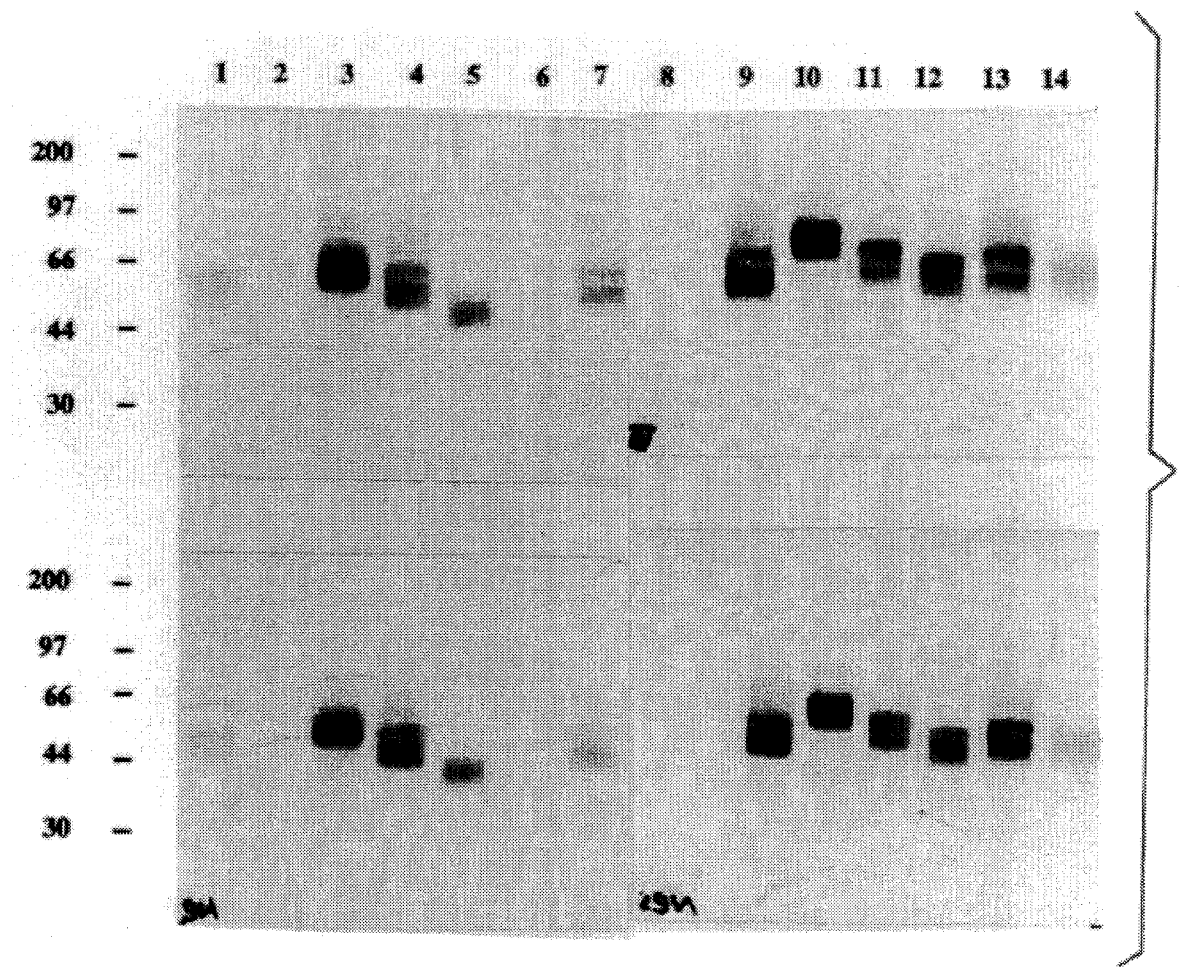

Analysis of lysostaphin digests of MRSA membrane fractions revealed that only the MRSA-aggl⁻ strains contained a protein having an approximate molecular weight of 230 KDa. That protein was not visualized in agglutination-positive strains as shown in FIGS. 1A and 1B; wherein the arrow indicates the MRSA-230 protein not detected by MRSA-aggl⁺ strains. Molecular weight markers are shown on the left of the Figures. FIG. 1A shows that digests of 11/14 MRSA-aggl⁻ strains contain an approximately 230 KDa protein band (lanes 1–11) which was not visualized in digests of agglutination-positive strains (lanes 1–14 in FIG. 1B). One MRSA-aggl⁻ strain showed a band at approximately 195 kDa (FIG. 1A, lane 12) and in two digests, no corresponding band was evident (FIG. 1A, lanes 13 and 14).

The products of lysostaphin digests, which contained the MRSA-230 protein were then 5× concentrated and purified. Purification was accomplished by first subjecting the digests to gel filtration using Sephacryl S-300 HR gel in 50 mM Na-phosphate/ 500 mM NaCl with 0.1 mM EDTA (ethylene diamine tetraacetic acid), 0.1 mM DDT (dithiothreitol), 0.1 mM PMSF (phenyl methyl sulfonyl fluoride), 0.1 mM Bentsamidine, and 0.15 mM N-ethylmaleimide. Fractions determined on the basis of SDS-PAGE as containing the MRSA-230 protein were pooled and concentrated using partial lyophilization.

Concentrated gel filtration pools were then analyzed by ion exchange chromatography using a Mono-Q 5/5 column with a buffer A comprising 50 mM Tris-HCl, pH 8.0 (buffer A) and a buffer B comprising buffer A plus 1M NaCl with a gradient of 0–60%. Fractions containing the MRSA-230 protein eluted at 420 to 580 mM NaCl and those fractions were pooled for hydrophobic interaction chromatography.

Hydrophobic interaction chromatography utilized a phenyl-sepharose 5/5 HR column, buffer A comprising 50 mM Na-phosphate, 4.0M NaCl, pH 7.0 with a gradient form 100% to 0, and buffer B comprising 50 mM Na-phosphate, pH 7.0. Only the MRSA-230 protein and its degradation products (see below) were detected in the eluate under the aforestated conditions. Accordingly, the flow-through fractions contained the MRSA-230 protein. However, it was noticed that a separate flow-through fraction contained another protein, having an approximate molecular weight of 175 kDa, was observed in the flow-through fraction. That protein was determined to be due to proteolytic degradation of MRSA-230 because anti-MRSA-230 antibodies reacted with the 175 kDa protein. The pool containing MRSA-230 was lyophilized by freezing to −70 ° C. and transferring to a room-temperature vacuum.

The purified, lyophilized MRSA-230 protein was then reduced by first adding 15–20 μg aliquots of the purified fractions to a solution containing 0.5M Tris-HCl, pH 7.5, 6M guanidine-HCl, and 2M EDTA and then immediately adding 5 μl of 0.4M DTT. The mixture was allowed to incubate for 10 minutes at 20° C. Alkylation was next performed by adding 1 μl 4-vinyl pyridine to the above mixture and incubating for 10 minutes at 20° C. By-products of the reducing and alkylating steps were then removed by reverse-phase C4 chromatography and the MRSA-230 protein was digested by addition of 50 μl 0.1M ammonium bicarbonate and 0.2 μl trypsin followed by 1 hour incubation at 37° C., and then addition of 0.5 μl trypsin (0.5 mg/ml) in 10 mM HCl and incubation overnight at 37° C.

The MRSA-230 peptide fragments produced by tryptic digestion were then characterized by high performance liquid chromatography using an Applied Biosystems 400 solvent delivery system, a 490 dynamic mixer, and 783A programmable detector on an RP Vydac 214TP52-C4 column (4.6× 25 mm) according to the Manufacturer's instruction. The tryptic digestion of purified and reduced MRSA-230 protein produced seven identifiable peptide sequence fractions of MRSA-230.
These are:
Thr-Thr-Thr-Pro-Thr-Thr-Ile-Asn (SEQ ID NO: 1)
Pro-Tyr-Ala-Xaa-Phe-Val (SEQ ID NO: 2)
Gln-Pro-Pro-Leu-Glu-Pro-Ser (SEQ ID NO: 3)
Xaa-Phe-Asn-Pro-Asp-Leu-Lys-Pro (SEQ ID NO: 4)
Glu-Pro-Glu-Thr-Gly-Glu-Val-Val-Thr-Pro-Pro-Asp (SEQ ID NO: 5)
Asp-Gly-Arg (SEQ ID NO: 6)
Asp-Ala-Leu-Ala-Ile-Ala-Gly-Ala-Gly (SEQ ID NO: 7).

The skilled artisan recognizes that standard techniques in the art may be used to generate a set of oligonucleotide probes, based upon the above sequence fragments, which may be used to probe a library of cDNA from methicillin-resistant *S. aureus* which do not test positive on standard slide agglutination tests in order to isolate, clone, and sequence of the gene(s) encoding MRSA-230, and thereby deduce the predicted amino acid sequence of MRSA-230.

EXAMPLE 4

Characteristics of The MRSA-230 Protein

The 230 KDa protein (MRSA-230 protein) isolated as described above was analyzed by immunoblotting. Rabbits were immunized with MRSA-aggl$^-$ bearing the MRSA-230 protein and agglutination positive strains in the manner described above.

The results are shown in FIGS. 2A and 2B, wherein Molecular weight markers are provided on the left side of the Figure. Anti-MRSA-230 antibodies absorbed with *S. epidermidis* principally visualized the 230 KDa MRSA-230 protein and a 175 KDa protein, which was probably due to proteolytic degradation of the 230 KDa protein (FIG. 2A). Neither the 230 KDa nor the 175 KDa proteins were observed in digests of MRSA strains which displayed positive agglutination tests. Other minor bands were detected in immunoblots of MRSA-aggl$^-$ strains (FIG. 2A, lanes 1–11). One polypeptide band was visualized with control serum (FIG. 2B) but control serum produced no bands in the region of the 230 KDa protein or its suspected degradation products.

EXAMPLE 5

Direct Agglutination Assay Using Anti-MRSA-230 Antibodies

Direct agglutination assays, as provided above, were performed in which rabbit antiserum was obtained by immunization with MRSA-aggl$^-$ strains absorbed with *S. epidermidis* and with purified anti-MRSA-230 antibodies. Direct bacterial agglutination assays were performed by mixing 2–3 colonies of *Staphylococci* with absorbed and 1:7 diluted anti-MRSA-aggl$^-$ antiserum or with concentrated purified anti-MRSA-230 antibodies on a coverslip. Agglutination was recorded after 10–30 seconds. Serum from nonimmunized rabbits was used as a control.

The results are shown in Table 2. As shown, anti-MRSA-aggl $^-$ antiserum detected all the MRSA-aggl$^-$ strains and 64/65 positive strains. None of 52 *S. epidermidis* strains also tested were detected as positive, even though they were all methicillin-resistant. In a separate test, purified anti-MRSA-230 antibodies detected all 14 MRSA-aggl$^-$ strains. These results show that anti-MRSA-230 antibodies detect methicillin-resistant strains of *S. aureus* with high specificity and, further, that anti-MRSA-230 antibodies, or serum containing them, detects methicillin-resistant *S. aureus* strains not detected by standard methods (see above).

TABLE 2

| | Direct Agglutination Assay | | | |
|---|---|---|---|---|
| | | Agglutination Antiserum | | |
| Strain | No. | anti-MRSA-aggl$^-$ | anti-230 | NRS |
| MSSA | 32 | 20 | NT | 0 |
| MRSA-aggl$^-$ | 14 | 14 | 14 | 0 |
| MRSA-aggl$^+$ | 65 | 64 | 0 | 0 |
| *S. epidermidis* | 52 | 0 | NT | 0 |
| Coagulase Neg. *Staphylococci* | 16 | 1 | NT | 0 |

In Table 2, MRSA-aggl$^+$ indicates strains which tested positive for *S. aureus* in standard slide agglutination tests; NT designates antisera not tested, and MSSA designates strains which were methicillin-sensitive *S. aureus*. These results demonstrate that anti-MRSA-230 antibodies specifically detect those methicillin-resistant strains of *S. aureus* which were not detected (i.e., gave false negative results) in conventional slide agglutination assays and that anti-MRSA-aggl$^-$ antiserum detects nearly all strains of *S. aureus,* whether or not such strains produce positive results in standard slide agglutination test.

The MRSA-230 protein is a unique *S. aureus* protein and appears not to be related to other known protein factors in *S. aureus.* Other cell surface proteins, such as the 48 kDa pentaglycine cross-linking protein and the 74 kDa penicillin-binding protein have molecular weights considerably lower than MRSA-230. Accordingly, the MRSA-230 is a unique marker for *S. aureus* and effectively detects methicillin-resistant strains when standards assays of the art do not.

Although the present invention has been described in terms of preferred embodiments thereof, the skilled artisan realizes that variations and improvements will occur to those of ordinary skill in the art upon consideration of the present invention. Therefore, it is intended that the appended claims embrace their equivalence and that only such limitations as are contained in the following claims and their equivalents should be read into the present invention.

We claim:

1. A method for detection of *Staphylococcus aureus* in a sample, comprising the steps of:
   (a) culturing a sample suspected of containing *S. aureus*,
   (b) mixing colonies resulting from step (a) with MRSA aggl⁻ antiserum which is produced by immunization with methicillin-resistant *S. aureus* (MRSA) bacteria which do not agglutinate in standard agglutination tests; and
   (c) detecting agglutination, wherein the presence of agglutination indicates the presence of *S. aureus* in the sample.

2. The method according to claim 1, wherein said mixing and detecting steps comprise a direct agglutination assay.

3. The method according to claim 1, wherein said MRSA aggl⁻ antiserum is rabbit antiserum.

4. A kit for identification and detection of methicillin-resistant *Staphylococcus aureus* comprising a formulation of antibodies which specifically bind MRSA-230 in an acceptable carrier.

5. A method for detecting a methicillin-resistant strain of *Staphylococcus aureus* in a sample, comprising the steps of:
   (a) culturing a sample suspected of containing methicillin-resistant *S. aureus*,
   (b) mixing colonies resulting from step (a) with antibodies which specifically bind MRSA-230; and
   (c) detecting agglutination, wherein the presence of agglutination indicates the presence of a methicillin-resistant strain of *Staphylococcus aureus* which is not detected in standard agglutination assays.

6. The method according to claim 5 wherein said antibodies are monoclonal antibodies.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:1:

Thr Thr Thr Pro Thr Thr Ile Asn
 1        5

( 2 ) INFORMATION FOR SEQ ID NO:2:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:2:

Pro Tyr Ala Xaa Phe Val
 1      5

( 2 ) INFORMATION FOR SEQ ID NO:3:

( i ) SEQUENCE CHARACTERISTICS:
    ( A ) LENGTH: 7 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:3:

Gln Pro Pro Leu Glu Pro Ser
 1      5

( 2 ) INFORMATION FOR SEQ ID NO:4:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:4:

Xaa Phe Asn Pro Asp Leu Lys Pro
 1      5

( 2 ) INFORMATION FOR SEQ ID NO:5:

( i ) SEQUENCE CHARACTERISTICS:
    ( A ) LENGTH: 12 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:5:

Glu Pro Glu Thr Gly Glu Val Val Thr Pro Pro Asp
 1    5        10

( 2 ) INFORMATION FOR SEQ ID NO:6:

( i ) SEQUENCE CHARACTERISTICS:
    ( A ) LENGTH: 3 amino acids
    ( B ) TYPE: amino acid (D) TOPOLOGY: linear (ii) MOLECULE TYPE: peptide (xi) SEQUENCE DESCRIPTION: SEQ ID NO:6:

Asp Gly Arg
 1

(2) INFORMATION FOR SEQ ID NO:7:

(i) SEQUENCE CHARACTERISTICS:
    (A) LENGTH: 9 amino acids
    (B) TYPE: amino acid
    (D) TOPOLOGY: linear (ii) MOLECULE TYPE: peptide (xi) SEQUENCE DESCRIPTION: SEQ ID NO:7:

Asp Ala Leu Ala Ile Ala Gly Ala Gly
 1               5